United States Patent
Held et al.

(10) Patent No.: US 12,044,352 B2
(45) Date of Patent: Jul. 23, 2024

(54) FLOOR STAND AND OPTICAL DETECTION APPARATUS HAVING SUCH A FLOOR STAND

(71) Applicant: Carl Zeiss Meditec AG, Jena (DE)

(72) Inventors: Jürgen Held, Rechberg (DE); Lennart Blatt, Coburg (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 18/115,829

(22) Filed: Mar. 1, 2023

(65) Prior Publication Data
US 2023/0313939 A1 Oct. 5, 2023

(30) Foreign Application Priority Data
Mar. 14, 2022 (DE) ..................... 10 2022 105 921.9

(51) Int. Cl.
*F16M 11/20* (2006.01)
*F16M 11/06* (2006.01)
*G02B 7/00* (2021.01)

(52) U.S. Cl.
CPC ......... *F16M 11/2071* (2013.01); *F16M 11/06* (2013.01); *G02B 7/001* (2013.01); *F16M 2200/08* (2013.01)

(58) Field of Classification Search
CPC ............... F16M 11/2071; F16M 11/06; F16M 2200/08; G02B 7/001
USPC ... 248/688, 123.2, 182.1, 331, 274.1–297.51
See application file for complete search history.

(56) References Cited

U.S. PATENT DOCUMENTS

| 3,087,276 A | * | 4/1963 | Chauvelot | A47B 27/08 248/454 |
| 3,757,761 A | * | 9/1973 | Izuta | F41B 5/1426 124/23.1 |
| 6,532,108 B1 | * | 3/2003 | Pensel | G02B 21/0012 359/384 |
| 2002/0064048 A1 | * | 5/2002 | Sander | A61B 90/35 248/123.11 |
| 2004/0160667 A1 | * | 8/2004 | Sander | G02B 7/001 359/368 |

(Continued)

FOREIGN PATENT DOCUMENTS

DE 10 2011 003 589 8/2012

OTHER PUBLICATIONS

German Office Action for Application No. 10 2022 105 921.9 mailed Jan. 10, 2023 (14 pages).

*Primary Examiner* — Christopher Garft
(74) *Attorney, Agent, or Firm* — NIXON PEABODY LLP; Jeffrey L. Costellia (57) ABSTRACT

The invention relates to a floor stand for an optical detection device, having a foot part comprising multiple bearing points or a planar standing surface that span a base plane, having a first stand arm which is pivotably connected to the foot part by a first joint on the foot part, and which is connected to a second stand arm by a second joint remote from the foot part, wherein the length of the first stand arm is dimensioned such that the distance between the base plane and the second joint is smaller than the sum of the maximum value for the eye level when seated and the maximum value for the length of the lower leg including the foot when the first stand arm is aligned at 45 degrees in relation to the base plane.

16 Claims, 6 Drawing Sheets

(56) References Cited

U.S. PATENT DOCUMENTS

| | | | |
|---|---|---|---|
| 2013/0313382 A1 | 11/2013 | Jakubczak | |
| 2014/0291457 A1* | 10/2014 | Rotheisler | G03B 17/561 248/123.2 |
| 2017/0165026 A1* | 6/2017 | Voigt | A61B 90/50 |
| 2018/0168767 A1* | 6/2018 | Hirose | G02B 21/24 |
| 2019/0046283 A1* | 2/2019 | Nagao | B25J 19/0004 |
| 2021/0093411 A1 | 4/2021 | Hirose | |
| 2021/0333821 A1* | 10/2021 | Zarnowitz | F16M 11/2028 |

* cited by examiner

FLOOR STAND AND OPTICAL DETECTION APPARATUS HAVING SUCH A FLOOR STAND

CROSS-REFERENCE TO RELATED APPLICATIONS

The present application claims priority under 35 U.S.C. § 119 to German Patent Application No. 10 2022 105 921.9, filed Mar. 14, 2022, the contents of which are incorporated by reference herein in their entirety.

The invention relates to a floor stand for an optical detection apparatus, wherein the floor stand comprises a foot part, which comprises multiple bearing points or a planar standing surface that span a base plane. The floor stand moreover comprises a first stand arm, which is connected to the foot part by a first joint on the foot part, and which is connected to a second stand arm by a second joint remote from the foot part. The invention furthermore relates to an optical detection apparatus having such a floor stand and an optical detection device.

A floor stand, that is to say a stand set on the floor, is known from the Applicant's DE 10 2011 003 589 A1, for example. This floor stand has proven to be very good in practice. This floor stand is used, for example, to hold a surgical microscope and to spatially position it.

In a typical treatment or surgery scenario in which such a floor stand is used, the patient usually lies on a height-adjustable operating table. Adjustment ranges for its tabletop can amount to 60 centimetres (cm) to 110 cm, or 80 cm to 110 cm. The body of the patient and the way it is supported with cushions on the operating table and the nature of the surgical intervention require a further height, for example 15 cm or 20 cm, to be taken into consideration. A surgeon's chair can likewise have a height-adjustable design, for example in a height-adjustment range of 48 cm to 68 cm. If the surgeon is a relatively short person, footrests can be used.

The location of the surgical intervention is also the location which the surgeon wishes to observe through an optical detection device. This location can be referred to as the surgeon's operating region. Optical detection devices have a certain focal length or a certain focal length range in order to focus, that is to say sharply image, the operating region or a detail thereof. Typically, such focal lengths require there to be a distance of 200 millimetres (mm) to 600 mm between the operating region and the front lens of the optical detection device. This distance is at the same time also the space available to the surgeon below the front lens of the optical detection device for the purpose of making the intervention with their instruments, while the optical detection device supplies an enlarged image of the operating region to the surgeon.

The seated or else standing surgeon must observe the image of the optical detection device on a monitor while they are working with the instruments. Therefore, a necessary condition for ergonomic working is that the view of such a monitor is not restricted by the optical detection device or its stand. The starting point of the present invention is thus the use of a floor stand on which an optical detection device, for example in the form of a digital microscope camera, can be mounted. In this respect—by contrast to surgical microscopes having an eyepiece—the user does not have to look through such an eyepiece themselves in order to observe the optically detected region. The image is shown to the user "externally" on a screen.

The object of the present invention is to provide a floor stand for which the field of view of a seated or else standing user is less restricted by stand elements. It is furthermore the object of the invention to specify a corresponding optical detection apparatus having such a floor stand.

This object is achieved by a floor stand having the features of claim 1 and by an apparatus having the features of claim 11. Advantageous embodiments with expedient refinements of the invention are specified in the dependent claims.

The floor stand according to the invention is distinguished in particular in that the length of the first stand arm is dimensioned such that the distance between the base plane and the second joint is smaller than the sum of the maximum value for the eye level when seated in accordance with DIN 33402-2—December 2020 and the maximum value for the length of the lower leg including the foot (seat surface height) in accordance with DIN 33402-2—December 2020 when the first stand arm is aligned at 45 degrees in relation to the base plane.

The multiple bearing points or the planar standing surface of the foot part are those that span an imaginary base plane. This base plane is therefore that plane which, when the floor stand is being used as intended, corresponds to the floor on which the floor stand is set.

The floor stand according to the invention is linked to the advantage that a standing, and in particular also a seated user has an unrestricted view beyond the now lower-down stand elements of the floor stand. This is conducive, for example, to the view of monitors set up separately from the floor stand, on which monitors the image captured by the optical detection device is reproduced. If the floor stand is used in medical surgery, it is conventional, for example in ear, nose and throat surgery or dental surgery or brain surgery, for a surgeon and an assistant together to be working while seated, and for them to be able to be on different sides of the stand elements. In other words, the stand elements are located between the two persons. In the case of the now-selected configuration of the floor stand, their line of sight is not blocked by stand elements.

DIN 33402-2 (as of: December 2020) is concerned with human body dimensions. In this standard, the sum of the maximum value for the eye level when seated and the maximum value for the length of the lower leg including the foot adds up to approximately 1.40 metres. It has been found that this value contributes to the floor stand being particularly ergonomic for a user.

In order to ensure that the line of sight to monitors or to other persons remains free in as many positions of the floor stand as possible, it has proven to be advantageous when the length of the first stand arm is dimensioned such that the distance between the base plane and the second joint is smaller than the sum of the maximum value for the eye level when seated in accordance with DIN 33402-2—December 2020 and the maximum value for the length of the lower leg plus the foot in accordance with DIN 33402-2—December 2020 when the first stand arm is aligned perpendicularly in relation to the base plane.

The first stand arm and the second stand arm in particular have a straight form. It has proven to be advantageous when the first stand arm is as long as possible, because this offers the advantage of positioning the optical detection device as easily and precisely as possible, in particular over a wide range on flat curved paths. For this reason, it has been shown to be advantageous when the first stand arm is between 0.80 metres and 1.20 metres long. The length of the first stand arm is preferably between 0.90 metres and 1.10 metres, particularly preferably substantially 1.0 metres. These designs favourably also force the first joint on the foot part to be positioned close to the floor, because this results in a lower down centre of gravity of the floor stand. The first joint, close to the floor, on the foot part in this way is located at a distance of between 0.10 metres and 0.50 metres from the base surface, therefore from the floor. The distance between the first joint on the foot part and the base surface is preferably between 0.20 metres and 0.40 metres, particularly preferably substantially 0.30 metres.

The "distance" in relation to the base plane should always be understood as meaning the smallest possible distance. The distance between the first joint and the base plane is thus measured along the normal of the base plane, therefore of the floor, that runs through the first joint, close to the floor, in the respective position of the floor stand. The distance between the second joint and the base plane is thus measured analogously along the normal of the base plane, therefore of the floor, that runs through the central, second joint in the respective position of the floor stand.

As a result of the solution according to the invention, the optical detection device and the articulated arm fastened thereto are below a conical field of view pointing from the eye of the surgeon to the monitor.

The eye levels of persons when seated, depending on the body height and body proportion, can be between 70 cm and 85 cm above the seat surface, for example. A typical chair height of the operating chair of 48 cm to 68 cm results in a possible eye level range when seated, as measured from the floor, of 118 cm to 153 cm. When standing, the eye level range is from 145 cm to 180 cm. These and all other anthropometric values are estimated using the values from DIN 33402.

It should be taken into consideration that the optical detection device and the articulated arm fastened thereto are several centimetres, e.g. 10 cm or 15 cm, in front of the eye of the surgeon. This means that the conical field of view, from the eye, of the seated or standing surgeon has already widened somewhat. The optical detection device and the articulated arm fastened thereto must be far enough below the eye level at this location.

For an ergonomic workspace and working process, it is necessary for the surgeon to be able to work with their instruments in the operating region with their body posture as relaxed and as free of fatigue as possible. To that end, the operating region, depending on the size of the instruments used, must be located at or below the elbow height of the surgeon. When standing, this elbow height can be approximately 98 cm to 120 cm, depending on the body height, additional height caused by the shoes, and body proportion of the surgeon. When seated, this elbow height can be approximately 20 to 30 cm, measured as a height above the seat surface.

Four selected use scenarios follow in order to explain the relationships between the surgeon, their work equipment (operating table, operating chair, floor stand, optical detection device, instruments, monitors) and the patient (operating region).

1. First of all, a scenario of a surgeon who is a seated, short person with a body height of approximately 154 cm is supposed. In this respect, the operating table height is set to the minimum value of 60 cm from the floor. In this scenario, the operating region is at a height of approximately 75 cm (60 cm table height+15 cm patient height). The elbow height of the short, seated surgeon is approximately 20 cm above the seat surface height (see: elbow height above the seat surface in accordance with DIN 33402-2—December 2020). In this case, an operating chair height of 55 cm is necessary in order to be able to work approximately at elbow height. The feet of the short surgeon must be supported by a footrest. The eye level is approximately 70 cm above the seat surface level. The eye level above the floor is approximately 125 cm (70 cm seat surface+55 cm chair height). The focal length of the optical detection device is 230 mm, for example. The structural length of the optical detection device as far as the articulated connection to the second stand arm is approximately 25 cm. In this respect, the articulation point level of the second joint at the end of the second stand arm should correspond to the height of the operating region plus the parameters given by the optical detection device, in the present case specifically approximately 123 cm (75 cm operating region height+23 cm focal length+25 cm structural length).

In this first scenario, for example, use is made of a floor stand, the first arm of which has a length of approximately 100 cm, which is arranged in an articulated manner approximately 30 cm above the floor, and the second arm of which has a length of approximately 75 cm. In this configuration, surgeons who are short persons can set the floor stand such that the first stand arm is inclined by 80 degrees in relation to the base plane, and the second stand arm is inclined by 4 degrees in relation to the base plane (below the horizontal) in the opposite direction. In mathematical terms, this configuration results in the desired height of the second joint being approximately 123 cm. The second joint thus lies below the eye level of the short surgeon, which is 125 cm.

2. The scenario of a surgeon who is a seated, tall person with a body height of approximately 186 cm is also dealt with. In this respect, the operating table height is set to a value of 80 cm from the floor. In this scenario, the operating region is at a height of approximately 95 cm (80 cm table height+15 cm). The elbow height of the tall, seated surgeon is approximately 30 cm above the seat surface height. In this case, an operating chair height of 60 cm is necessary in order to be able to work approximately at elbow height. The eye level is approximately 85 cm above the seat surface level. The eye level above the floor is approximately 145 cm (85 cm seat surface+60 cm chair height). The focal length of the optical detection device is 230 mm, for example. The structural length of the optical detection device as far as the articulated connection to the second stand arm is approximately 25 cm. In this respect, the articulation point level of the second joint at the end of the second stand arm should correspond to the height of the operating region plus the parameters given by the optical detection device, in the present case specifically approximately 143 cm (95 cm operating region height+23 cm focal length+25 cm structural length).

In this second scenario, for example, use is made of a floor stand, the first arm of which has a length of approximately 100 cm, which is arranged in an articulated manner approximately 30 cm above the floor, and the second arm of which has a length of approximately 75 cm. In this configuration, surgeons who are tall persons can set the floor stand such that the first stand arm is inclined by 90 degrees in relation to the base plane, and the second stand arm is inclined by 10 degrees in relation to the base plane (above the horizontal) in the same direction. In mathematical terms, this configuration results in the desired height of the second joint being approximately 143 cm. The second joint thus lies below the eye level of the tall surgeon, which is 145 cm.

3. The scenario of a surgeon who is a standing, short person with a body height of approximately 154 cm is moreover dealt with. In this respect, for example, the operating table height is set to a value of 80 cm from the floor.

In this scenario, the operating region is at a height of approximately 95 cm (80 cm table height+15 cm). The elbow height of the short, standing surgeon is approximately 98 cm above the floor (see elbow height above the standing surface in accordance with DIN 33402-2—December 2020). The eye level is approximately 145 cm above the floor (see eye height in accordance with DIN 33402-2—December 2020). The focal length of the optical detection device is 230 mm, for example. The structural length of the optical detection device as far as the articulated connection to the second stand arm is approximately 25 cm. In this respect, the articulation point level of the second joint at the end of the second stand arm should correspond to the height of the operating region plus the parameters given by the optical detection device, in the present case specifically approximately 143 cm (95 cm operating region height+23 cm focal length+25 cm structural length).

In this third scenario, for example, use is made of a floor stand, the first arm of which has a length of approximately 100 cm, which is arranged in an articulated manner approximately 30 cm above the floor, and the second arm of which has a length of approximately 75 cm. In this configuration, surgeons who are short, standing persons can set the floor stand such that the first stand arm is inclined by 90 degrees in relation to the base plane, and the second stand arm is inclined by 10 degrees in relation to the base plane (above the horizontal) in the same direction. In mathematical terms, this configuration results in the desired height of the second joint being approximately 143 cm. The second joint thus lies below the eye level of the short, standing surgeon, which is 145 cm.

4. Lastly, the scenario of a surgeon who is a standing, tall person with a body height of approximately 186 cm is also dealt with. In this respect, for example, the operating table height is set to a value of 95 cm from the floor. In this scenario, the operating region is at a height of approximately 110 cm (95 cm table height+15 cm). The elbow height of the tall, standing surgeon is approximately 120 cm above the floor. The eye level is approximately 180 cm above the floor. The focal length of the optical detection device is 230 mm, for example. The structural length of the optical detection device as far as the articulated connection to the second stand arm is approximately 25 cm. In this respect, the articulation point level of the second joint at the end of the second stand arm should correspond to the height of the operating region plus the parameters given by the optical detection device, in the present case specifically approximately 158 cm (110 cm operating region height+23 cm focal length+25 cm structural length).

In this fourth scenario, for example, use is made of a floor stand, the first arm of which has a length of approximately 100 cm, which is arranged in an articulated manner approximately 30 cm above the floor, and the second arm of which has a length of approximately 75 cm. In this configuration, surgeons who are tall, standing persons can set the floor stand such that the first stand arm is inclined by 90 degrees in relation to the base plane, and the second stand arm is inclined by 22 degrees in relation to the base plane (above the horizontal) in the same direction. In mathematical terms, this configuration results in the desired height of the second joint being approximately 158 cm. The second joint thus lies below the eye level of the tall, standing surgeon, which is 180 cm.

On the basis of the statements made in the above scenarios, it has thus proven to be advantageous when the second stand arm is shorter than the first stand arm. This design makes it possible to collapse the floor stand, specifically even when the optical detection device is fastened to the second stand arm. With preference, the second stand arm thus has a length which corresponds to that of the first stand arm minus the dimensions of the optical detection device. In this way, the second stand arm is therefore not selected to be excessively small, so that the floor stand is not too close to a table or a patient to be treated. The second stand arm should also not be selected to be excessively long, since in that case the foot part is too far away from the table or from the patient and adjustment along the base plane is possible only with greater complexity.

In other words, the compactly collapsed "parked position" of the floor stand is thus beneficial when the sum of the length of the optical detection device and the length of the second stand arm corresponds to or is smaller than the length of the first stand arm.

In order to be able to displace the optical detection device fastened to the second stand arm as easily as possible in terms of its position, it has proven to be advantageous when the foot part has a first rotary joint, by way of which the first joint can be rotated about a first axis of rotation oriented perpendicularly in relation to the base plane.

As an alternative or in addition, it may be provided that the first stand arm itself has a second rotary joint, by way of which the second joint can be rotated about a second axis of rotation extending along the longitudinal axis of the first stand arm. This also makes it possible to spatially position the optical detection device particularly easily.

In order to be able to pivot the optical detection device on the second stand arm, it has also been shown to be expedient when a third joint is present at the free end of the second stand arm.

A further degree of freedom for spatially setting the optical axis of the optical detection device is provided when a third rotary joint, on which the optical detection device is then mounted, is connected to the third joint at the free end of the second stand arm.

For the protected accommodation of electronics components, for example for controlling the stand arms of the floor stand or else for controlling an optical detection device fastened to the stand, a housing may be assigned to the foot part, wherein in that case the first joint is arranged on the housing. The first joint is very close to the floor in this configuration, too. Here, there is the option for a first rotary joint assigned to the foot part to be present, which, in addition to the rotation of the first joint, also brings about the rotation of the housing about a first axis of rotation oriented perpendicularly in relation to the base plane or in relation to the floor. However, it is not absolutely necessary for the first joint to be mounted on the housing, and therefore there is the option for the housing to be present on the foot part separately from the first joint.

In order to keep the movement forces necessary for repositioning the optical detection device as low as possible, it has proven to be advantageous when a weight compensation device is assigned to the first joint. In this way, the weight compensation or balancing device is thus likewise very close to the floor, thereby additionally lowering the centre of gravity of the floor stand and thus increasing the stability. The weight compensation device may, for example by actively displacing a weight, for example by way of actuation using a control device, compensate the torques exerted by the stand arms.

A configuration of the weight compensation device that is simplified by a mechanical structure could alternatively, however, also be formed by two fastening struts extending from the first stand arm, of which each of the fastening struts is connected to a fastening point on the foot part by a spring.

The advantages, configurations and effects explained in connection with the floor stand according to the invention apply in the same way to the optical detection apparatus according to the invention, which is formed with such a floor stand and with an optical detection device fastened to the floor stand. The optical detection device may be, for example, a surgical microscope, a spotting scope, a digiscope or a digital microscope camera or the like.

The apparatus is preferably configured to output the image detected by the optical detection device to a screen, which is connected to the floor stand or arranged separately from the floor stand.

The low position of the first joint and the accommodation of the weight compensation or the balancing close to the floor result in a lowering of the centre of gravity of the floor stand or provide the apparatus in this way with ergonomically favourable free space for the configuration of a housing.

Further features, properties and advantages of the present invention are described in more detail below on the basis of embodiment variants and with reference to the appended figures. In this respect, all the features described above and below are advantageous both individually and in any desired combination. The embodiment variants described below are merely examples which, however, do not limit the subject matter of the invention. In the figures.

FIGS. 1 to 10 show a respective optical detection apparatus 200, which comprises a floor stand 100 and an optical detection device 202 fastened to the floor stand 100. The optical detection device 200 is in particular a surgical microscope or a digital microscope camera, and is fastened to the floor stand 100.

The floor stand 100 comprises a foot part 102, which in the present case is formed with movable rollers 134. These rollers 134 stand on the floor, the contact points with the floor forming the bearing points 104 of the floor stand 100. These bearing points 104 thus span a base plane 138, which corresponds to the floor when the floor stand 100 is being used as intended.

The floor stand 100 is formed with two arms, specifically a first stand arm 106 and a second stand arm 110. The first stand arm 106 is pivotably connected to the foot part 102 by a first joint 108 on the foot part. The pivot axis of the first joint 108 runs parallel to the base plane 138, or parallel to the floor. The second stand arm 110 is connected to the first stand arm 106 by a second joint 112 remote from the foot part 102. The pivot axis of the second joint 112 likewise runs parallel to the base plane, or parallel to the floor. Moreover, a third joint 118, the pivot axis of which is likewise aligned parallel to the base surface, or to the floor, is present at the free end of the second stand arm 110 on which the optical detection device 202 is mounted. Also shown is the option of mounting the optical detection device 202 on the second stand arm 110 via a third rotary joint 120, which is downstream of the third joint 118. In this respect, the axis of rotation of the third rotary joint 120 runs perpendicularly in relation to the pivot axis of the third joint 118. It should be noted that the third joint 118 and the third rotary joint 120 can also be combined in a single polyaxially movable joint, which enables both a pivoting movement and a rotational movement.

Figure 1:
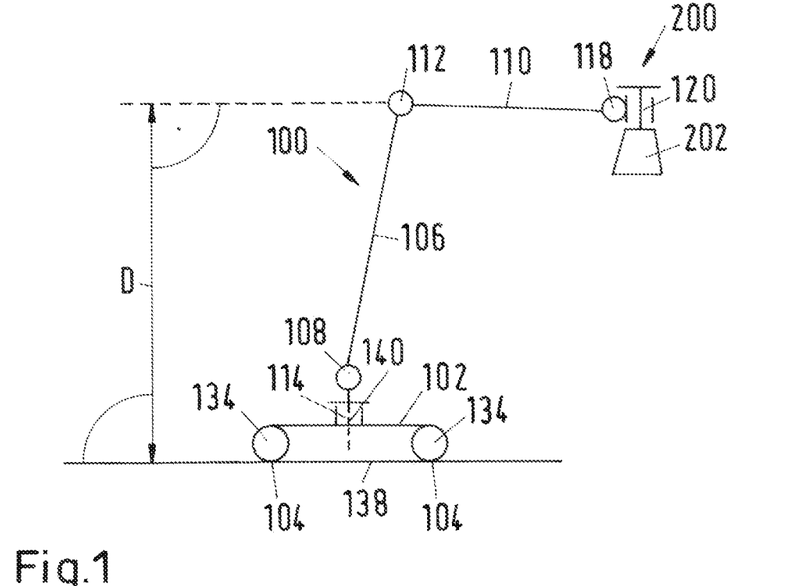
FIG. 1 shows a schematic illustration of an optical detection apparatus having a floor stand and an optical detection device fastened to the floor stand, with the floor stand being in a working position.

In the case of the floor stands 100 of FIGS. 1 to 10, the length of the first stand arm 106 is dimensioned such that the distance D between the base plane 138 spanned by the bearing points 104 and the second joint 112 is smaller than the sum of the maximum value for the eye level when seated in accordance with DIN 33402-2—December 2020 and the maximum value for the length of the lower leg including the foot in accordance with DIN 33402-2—December 2020 when the first stand arm 106 is inclined by 45 degrees in relation to the base plane 138. In the present case, the length of the first stand arm 106 is even dimensioned such that the distance D between the base plane 138 (or the floor) and the second joint 112 is smaller than the sum of the maximum value for the eye level when seated in accordance with DIN 33402-2—December 2020 and the maximum value for the length of the lower leg including the foot in accordance with DIN 33402-2—December 2020 when the first stand arm 106 is aligned perpendicularly in relation to the base plane 138. FIG. 1 illustrates this distance D, with the distance D of the second joint 112 forming the shortest connection to the floor (dropping a plumb line from the second joint 112).

In the present case, the length of the first stand arm 106 is between 0.80 metres and 1.20 metres, preferably between 0.90 metres and 1.10 metres, in particular substantially 1.00 metres. This results in the first joint 108 on the foot part being arranged very close to the floor and therefore being spaced apart from the base surface by a distance of between 0.10 metres and 0.50 metres, preferably between 0.20 metres and 0.40 metres, in particular substantially 0.30 metres.

Figure 2:
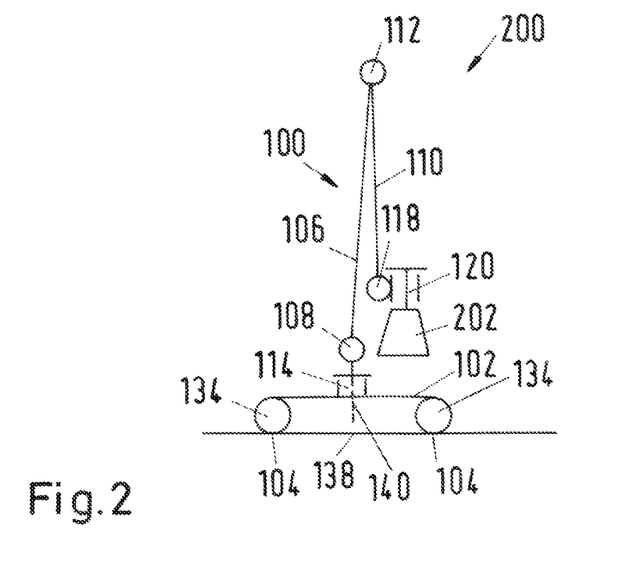
FIG. 2 shows a depiction corresponding to FIG. 1 of an optical detection apparatus, with the floor stand being in a rest position.

With reference to the depiction in FIG. 2, it can be seen that the second stand arm 110 is shorter than the first stand arm 106. In this way, the floor stand 100 can be collapsed very compactly when the optical detection device 202 is mounted on the second stand arm 110. The length of the second stand arm 110 preferably corresponds to the length of the first stand arm 106 minus the dimensions of the optical detection device 202.

Figure 3:
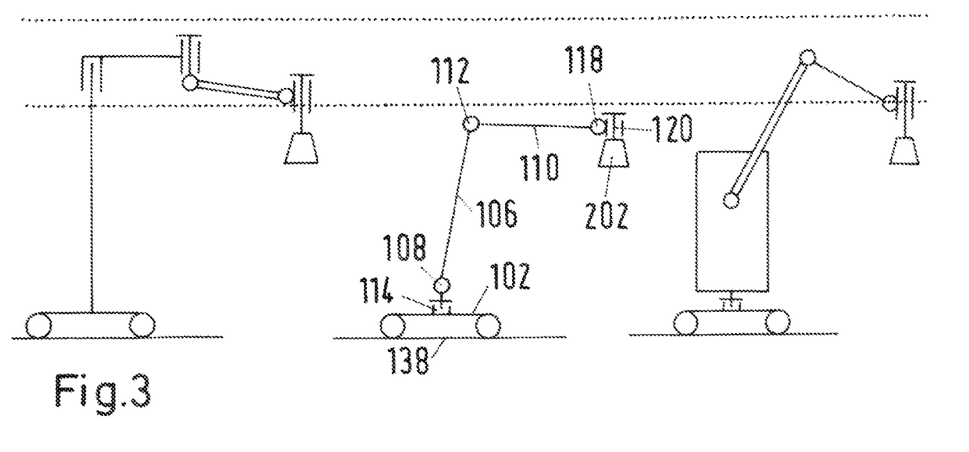
FIG. 3 shows the apparatus from FIGS. 1 and 2 in comparison with schematic illustrations of floor stands known from the prior art.

The thus selected length of the first stand arm 106 and the resulting arrangements of the first joint 108 and the second joint 112 result in the field of view of a seated user being kept largely free of stand elements, as illustrated by FIG. 3. Here, a comparison of traffic-light-like suspensions of known stands is shown on the left-hand and the right-hand side, with the centre showing the floor stand 100 designed according to the invention. The strip depicted by two dotted lines corresponds to the typical field of view of a seated user in this case. It can be seen that the known stands from the prior art have elements that project into this field of view. The view of a monitor would thus be restricted by stand parts of stands known from the prior art.

Figure 4:
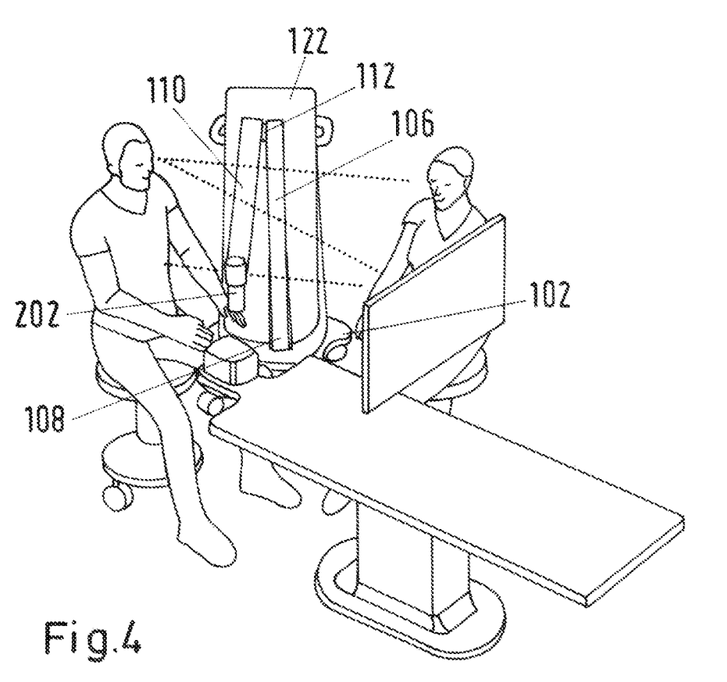
FIG. 4 shows a perspective depiction of a typical situation when using the optical detection apparatus and the associated floor stand.

FIG. 4 shows a typical situation when using the floor stand 100, or the optical detection apparatus 200, as arises for example during oral surgery. On account of the position of the second joint 112, the upper, second stand arm 110 is arranged such that the two persons participating in the surgery can see one another unobstructed, with the region below the second stand arm 110 being kept free, for example for exchanging tools. Moreover, the view of a monitor, schematically illustrated, is not obstructed by stand elements, and therefore the image detected by the optical detection device 202 can be viewed there by the seated persons.

In the case of the floor stands 100 of FIGS. 1 to 6 and 8 to 10, the foot part 102 has a first rotary joint 114, by way of which the first joint 108 can be rotated about a first axis of rotation 140 oriented perpendicularly in relation to the base plane 138, therefore in relation to the floor. FIG. 7 shows the option in which the first stand arm 106 itself has a second rotary joint 116, by way of which the second joint 112 can be rotated about a second axis of rotation 142 extending along the longitudinal axis of the first stand arm 106.

Figure 5:
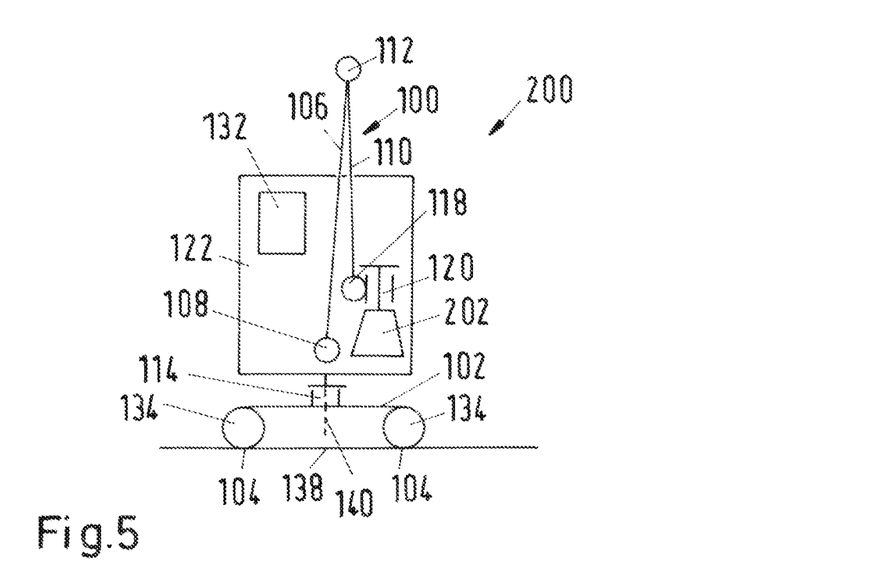
FIG. 5 shows a schematic illustration of an optical detection apparatus having a floor stand and an optical detection device, with the floor stand being formed with a housing and the joint on the foot part being arranged on the housing.
Figure 6:
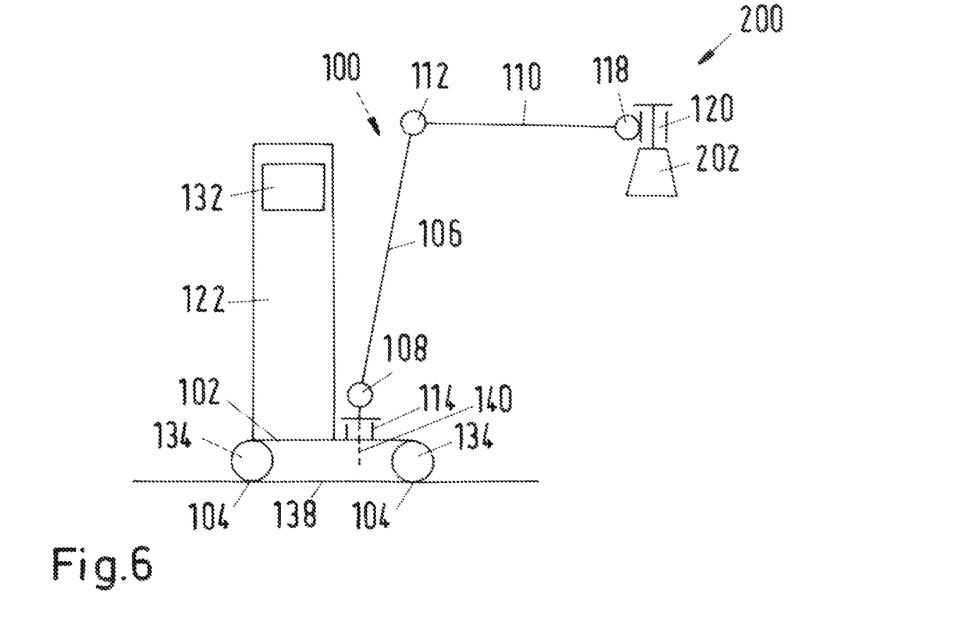
FIG. 6 shows a schematic illustration of an optical detection apparatus having a floor stand and an optical detection device, with the floor stand comprising a housing which is arranged separately from the first joint on the foot part.
Figure 7:
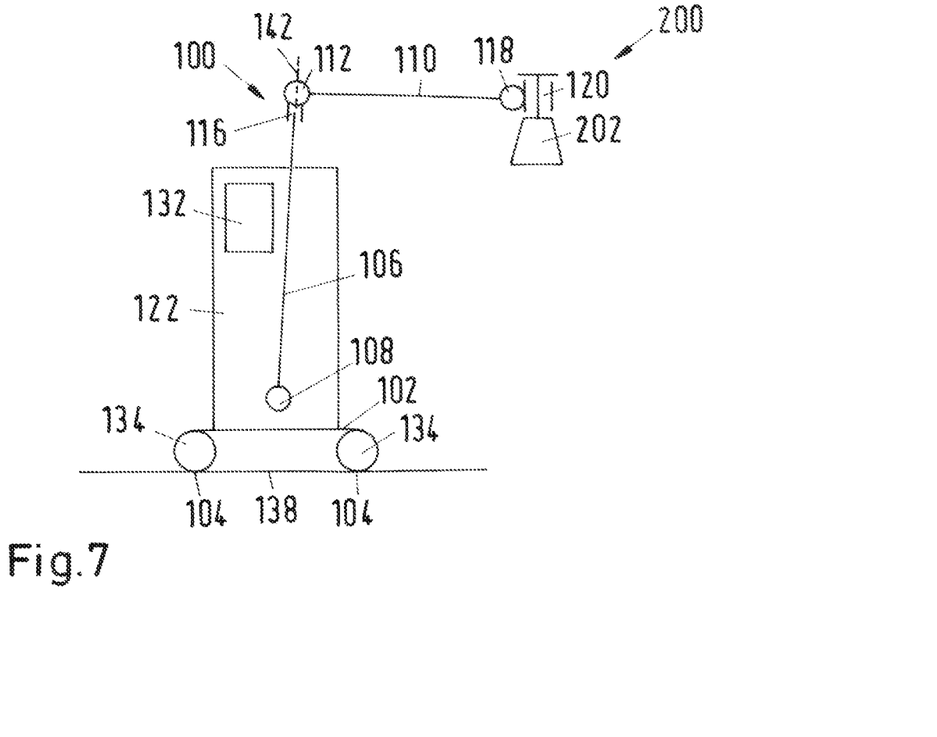
FIG. 7 shows a schematic illustration of an optical detection apparatus having a floor stand and an optical detection device, in the case of which a housing, on which the first joint on the foot part is arranged, is present, with an additional (second) rotary joint being assigned to the first articulated arm.

In the cases of the optical detection apparatuses 200 and the floor stands 100, present here, of FIGS. 4 to 6, a housing 122 is assigned to the foot part 102. While the first joint 108 is arranged on the housing 122 in the case of the floor stands 100 of FIGS. 4 and 5, the housing 122 is present on the floor part 102 separately from the first joint 108, which is close to the floor, in the case of the floor stand 100 according to FIG. 6. Moreover, in the case of the apparatuses 200 of FIGS. 4 and 5, the first rotary joint 114 is arranged such that the housing 122 can be rotated about a first axis of rotation 138 oriented perpendicularly in relation to the base surface, therefore in relation to the floor.

The housing 122 comprises electronics components, for example for controlling the optical detection device 202 or for setting the angular positions of the stand arms 106, 110 or else for setting the position of the joints 108, 112, 114, 118, 120. With preference, an operating unit 132 or else a display is additionally present on the housing 122. The housing 122 may moreover comprise a handle in order to be able to move the apparatus 200 on the floor.

Figure 8:
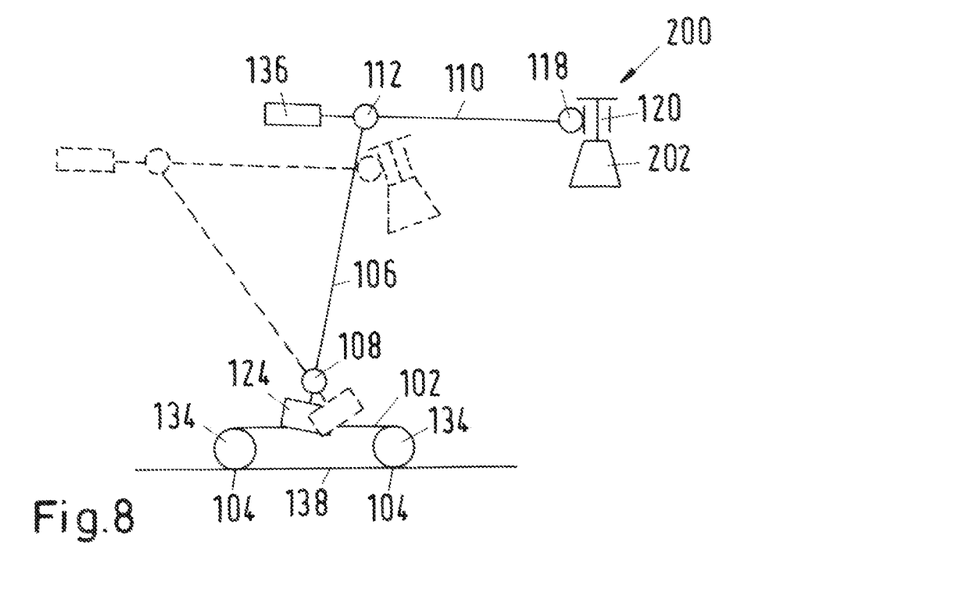
FIG. 8 shows a schematic illustration of an optical detection apparatus having a floor stand and an optical detection device according to FIGS. 1 and 2, with weight compensation devices being assigned to the floor stand.
Figure 9:
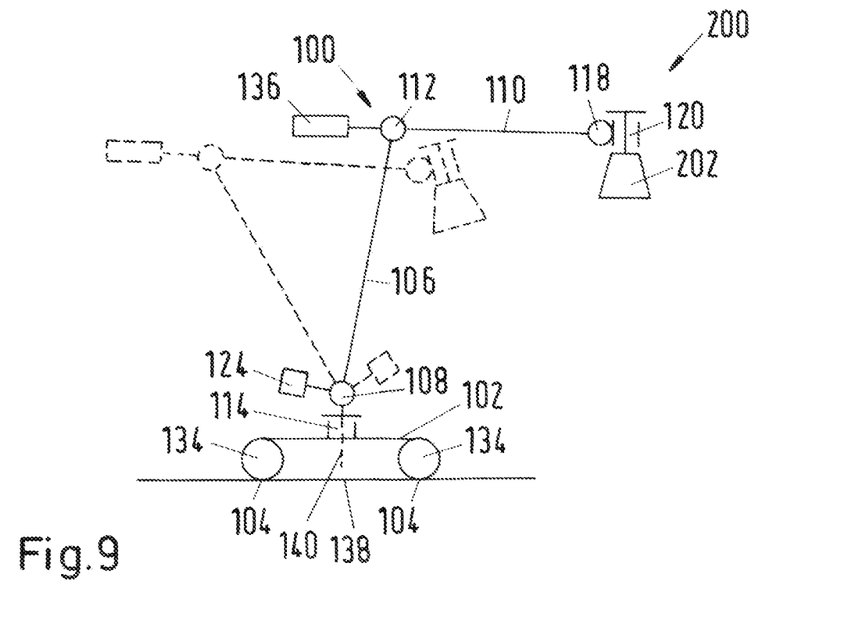
FIG. 9 shows a schematic illustration of an optical detection device according to FIGS. 1 and 2 with another configuration of the weight compensation device.
Figure 10:
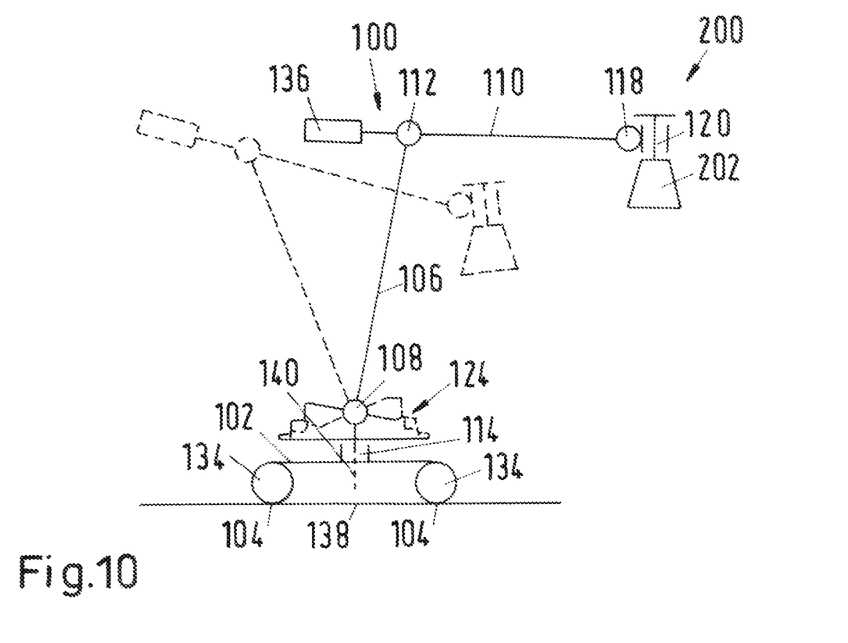
FIG. 10 shows a schematic illustration of the optical detection device according to FIGS. 1 and 2 with yet another, mechanical, configuration of the weight compensation device.

The floor stands 100 of FIGS. 8 to 10 are provided with weight compensation devices 124, 136. In the case of the floor stand 100 according to FIG. 8, a mass block engages on the first joint 108, which is close to the floor, and thus, by virtue of its inherent weight, at least partially compensates the torque exerted by the first stand arm 106. Moreover, a second weight compensation device 136, which at least partially compensates the torque acting on the second stand arm 110, is present.

The weight compensation device 124 in the case of the floor stand 100 according to FIG. 9 provides, for example, active motorized weight displacement that always has the effect of optimum weight compensation. In other words, in this respect, it is possible to use electromotive displacement of a mass for balancing.

Figure 11:
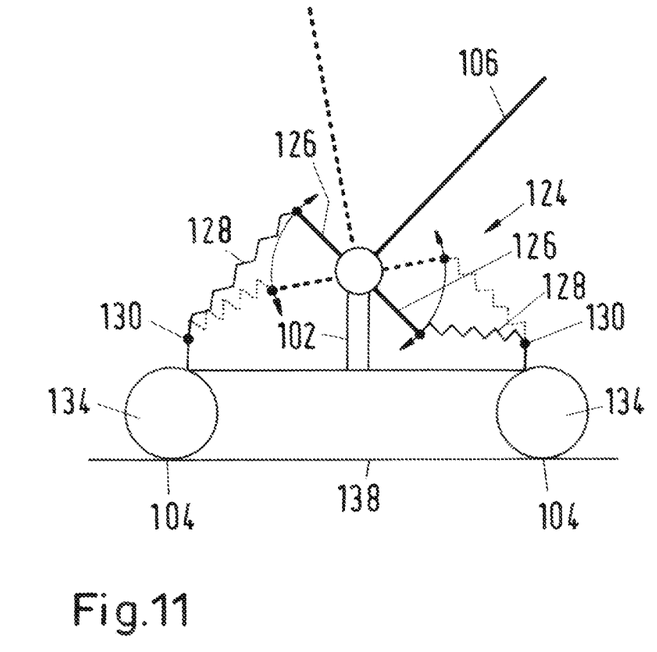
FIG. 11 shows a schematic view of a detail of the weight compensation device of the floor stand from FIG. 10.

A purely mechanical weight compensation solution is in FIG. 10. A detail thereof can be seen in FIG. 11. In this case, the weight compensation device 124 comprises two fastening struts 126 extending from the first stand arm 106. The fastening struts 126 are aligned at a predefined angle in relation to the first stand arm 106, in the present case are inclined by 90 degrees in relation to the first stand arm 106. Here, each of the fastening struts 126 is assigned a spring 128, which, at its end remote from the fastening strut 126, is connected to a fastening point 130 on the foot part 102.

As a result, the present invention is distinguished by its lower down stand elements, and therefore an unrestricted view of a monitor set up separately from the stand is possible. Even in situations in which it is necessary to interact with a surgical assistant, the field of view of the two seated persons is not restricted by stand elements. The positioning of the first joint 108 close to the floor additionally results in a favourable lowering of the centre of gravity of the stand and thus in a higher stability, in particular also when a weight compensation or balancing device 124 is additionally assigned to the first joint 108.

LIST OF REFERENCE SIGNS

100 Floor stand
102 Foot part
104 Bearing point/Bearing surface
106 First stand arm
108 First joint (on the foot part)
110 Second stand arm
112 Second joint (remote from the foot part)
114 First rotary joint
116 Second rotary joint
118 Third joint
120 Third rotary joint
122 Housing
124 Weight compensation device
126 Fastening strut
128 Spring
130 Fastening point
132 Operating unit
134 Roller
136 Second weight compensation device
138 Base plane
140 First axis of rotation
142 Second axis of rotation
200 Optical detection apparatus
202 Optical detection device

The invention claimed is:

1. A floor stand for an optical detection device, having a foot part comprising multiple bearing points or a planar standing surface that span a base plane, having a first stand arm which is pivotably connected to the foot part by a first joint on the foot part, and which is connected to a second stand arm by a second joint remote from the foot part, wherein the length of the first stand arm is dimensioned such that the distance between the base plane and the second joint is smaller than the sum of the maximum value for the eye height when seated in accordance with DIN 33402-2—December 2020 and the maximum value for the length of the lower leg including the foot in accordance with DIN 33402-2—December 2020 when the first stand arm is inclined by 45 degrees in relation to the base plane,
- wherein the length of the first stand arm is dimensioned such that the distance between the base plane and the second joint is smaller than the sum of the maximum value for the eye level when seated in accordance with DIN 33402-2—December 2020 and the maximum value for the length of the lower leg including the foot in accordance with DIN 33402-2 —December 2020 when the first stand arm is aligned perpendicularly in relation to the base plane,
- a weight compensation device is assigned to the first joint, and
- the weight compensation device comprises two fastening struts extending from the first stand arm, of which each of the fastening struts is connected to a fastening point on the foot part by a spring.

2. The floor stand according to claim 1, wherein the second stand arm is shorter than the first stand arm.

3. The floor stand according to claim 2, wherein the sum of the length of the optical detection device and the length of the second stand arm corresponds to or is smaller than the length of the first stand arm.

4. The floor stand according to claim 1, wherein the foot part has a first rotary joint, by way of which the first joint can be rotated about a first axis of rotation oriented perpendicularly in relation to the base plane.

5. The floor stand according to claim 1, wherein the first stand arm has a second rotary joint, by way of which the second joint can be rotated about a second axis of rotation extending along the longitudinal axis of the first stand arm.

6. The floor stand according to claim 1, wherein a third joint is present at the free end of the second stand arm.

7. The floor stand according to claim 1, wherein a housing is assigned to the foot part, and in that the first joint is arranged on the housing.

8. An optical detection apparatus, comprising a floor stand according to claim 1 and an optical detection device fastened to the floor stand.

9. A floor stand for an optical detection device, having a foot part comprising multiple bearing points or a planar standing surface that span a base plane, having a first stand arm which is pivotably connected to the foot part by a first joint on the foot part, and which is connected to a second stand arm by a second joint remote from the foot part, wherein the length of the first stand arm is dimensioned such that the distance between the base plane and the second joint is smaller than the sum of the maximum value for the eye height when seated in accordance with DIN 33402-2—December 2020 and the maximum value for the length of the lower leg including the foot in accordance with DIN 33402-2—December 2020 when the first stand arm is inclined by 45 degrees in relation to the base plane,
- wherein a weight compensation device is assigned to the first joint,
- wherein the weight compensation device comprises two fastening struts extending from the first stand arm, of which each of the fastening struts is connected to a fastening point on the foot part by a spring.

10. An optical detection apparatus, comprising a floor stand according to claim 9 and an optical detection device fastened to the floor stand.

11. The floor stand according to claim 9, wherein the second stand arm is shorter than the first stand arm.

12. The floor stand according to claim 11, wherein the sum of the length of the optical detection device and the length of the second stand arm corresponds to or is smaller than the length of the first stand arm.

13. The floor stand according to claim 9, wherein the foot part has a first rotary joint, by way of which the first joint can be rotated about a first axis of rotation oriented perpendicularly in relation to the base plane.

14. The floor stand according to claim 9, wherein the first stand arm has a second rotary joint, by way of which the second joint can be rotated about a second axis of rotation extending along the longitudinal axis of the first stand arm.

15. The floor stand according to claim 9, wherein a third joint is present at the free end of the second stand arm.

16. The floor stand according to claim 9, wherein a housing is assigned to the foot part, and in that the first joint is arranged on the housing.

* * * * *